US009334118B1

(12) United States Patent
Tanner

(10) Patent No.: US 9,334,118 B1
(45) Date of Patent: May 10, 2016

(54) AIR TREATMENT SYSTEMS AND METHODS

(71) Applicant: Prolitec Inc., Milwaukee, WI (US)

(72) Inventor: Howard Tanner, Wauwatosa, WI (US)

(73) Assignee: Prolitec Inc., Milwaukee, WI (US)

( * ) Notice: Subject to any disclaimer, the term of this patent is extended or adjusted under 35 U.S.C. 154(b) by 0 days.

(21) Appl. No.: 14/928,807

(22) Filed: Oct. 30, 2015

Related U.S. Application Data

(60) Provisional application No. 62/220,139, filed on Sep. 17, 2015.

(51) Int. Cl.
| | |
|---|---|
| *B65G 11/20* | (2006.01) |
| *B05B 15/06* | (2006.01) |
| *A61L 9/14* | (2006.01) |
| *B65G 45/22* | (2006.01) |
| *A61L 11/00* | (2006.01) |
| *B65F 7/00* | (2006.01) |
| *B65F 1/00* | (2006.01) |
| *E04F 17/12* | (2006.01) |

(52) U.S. Cl.
CPC ............... *B65G 11/203* (2013.01); *A61L 9/14* (2013.01); *A61L 11/00* (2013.01); *B05B 15/06* (2013.01); *B65F 1/0093* (2013.01); *B65F 7/00* (2013.01); *B65G 45/22* (2013.01); *E04F 17/123* (2013.01)

(58) Field of Classification Search
CPC .... B65G 11/20; B65G 11/203; B65G 11/206; B65G 45/22; A61L 11/00; A61L 9/14; A61L 9/145; B05B 15/06; B65F 1/0093; B65F 7/00; E04F 17/123; E04F 17/126
USPC ...................................................... 193/11, 34
See application file for complete search history.

(56) References Cited

U.S. PATENT DOCUMENTS

| | | | | | |
|---|---|---|---|---|---|
| 1,123,210 | A | * | 12/1914 | Shepherd ............. | B65G 11/126 141/383 |
| 1,169,302 | A | * | 1/1916 | Triggs ...................... | B65F 7/00 193/11 |
| 1,169,319 | A | * | 1/1916 | Dargin ................. | B65G 11/126 193/11 |
| 1,269,793 | A | * | 6/1918 | Dargin ................. | B65G 11/126 193/11 |
| 1,510,288 | A | * | 9/1924 | Malone ................ | B65G 11/186 193/34 |
| 1,739,534 | A | * | 12/1929 | Wilkinson .............. | E04F 17/12 193/34 |

(Continued)

OTHER PUBLICATIONS

U.S. Appl. No. 14/928,807, Keith R. Campbell.*

*Primary Examiner* — Leslie A Nicholson, III
*Assistant Examiner* — Keith R Campbell
(74) *Attorney, Agent, or Firm* — Seed IP Law Group PLLC

(57) ABSTRACT

A system is provided for treating a trash chute with an aerosolized compound. The system includes an aerosol discharge unit mounted to a door frame of a fire door arrangement of the trash chute with an aerosol outlet thereof in fluid communication with the trash passageway; a liquid diffusion appliance mounted remotely from the trash chute and the fire door arrangement, the liquid diffusion appliance including a compound in liquid form to be aerosolized and including a control system for operating the liquid diffusion appliance to generate the aerosolized compound from the liquid compound and to discharge the aerosolized compound from an appliance outlet of the liquid diffusion appliance; and a conduit coupling the appliance outlet of the liquid diffusion appliance with the aerosol outlet of the discharge unit, the conduit defining an aerosol passageway through which the aerosolized compound travels to be discharged into the trash chute.

21 Claims, 5 Drawing Sheets

(56) References Cited

U.S. PATENT DOCUMENTS

| | | | |
|---|---|---|---|
| 3,608,476 A * | 9/1971 | Price | B30B 9/3075 100/215 |
| 3,690,560 A * | 9/1972 | Boyd | E04F 17/126 118/306 |
| 3,695,172 A * | 10/1972 | Cleary | B30B 9/3078 100/215 |
| 3,926,107 A * | 12/1975 | Dunlap | A61L 11/00 100/215 |
| 4,002,229 A * | 1/1977 | Washington | A62C 2/06 141/98 |
| 4,578,185 A * | 3/1986 | Wilson | A61L 11/00 210/143 |
| 5,203,618 A * | 4/1993 | Oshall | B65F 1/067 220/495.08 |
| 7,017,728 B2 * | 3/2006 | Nyquist | E04F 17/12 193/33 |
| 7,712,683 B2 | 5/2010 | Robert et al. | |
| 7,930,068 B2 | 4/2011 | Robert et al. | |
| 8,523,051 B2 * | 9/2013 | Clancy | B65F 1/0093 193/34 |
| 8,855,827 B2 | 10/2014 | Weening et al. | |

* cited by examiner

AIR TREATMENT SYSTEMS AND METHODS

BACKGROUND

1. Technical Field

The present disclosure relates generally to air treatment systems and methods and, more specifically, to air treatment systems and methods for treating a trash chute with an aerosolized compound generated by a liquid diffusion appliance that is located remote from the trash chute.

2. Description of the Related Art

Liquid diffusion appliances are known which have the ability to dispense scent or other aerosolized matter throughout the atmosphere of a desired space and have been used to heavily treat a trash room or other space in which a trash chute is present such that some scent is drawn into the chute. Such systems, however, are generally ineffective in treating the chute itself and are inefficient in terms of the liquid scent compound consumed during treatment.

BRIEF SUMMARY

The air treatment systems and methods described herein enable treating a trash chute with an aerosolized compound generated by a liquid diffusion appliance that is located remote from the chute in a particularly effective and non-disruptive manner.

At least one embodiment of a system for treating a trash chute with an aerosolized compound may be summarized as including: a trash chute having a tubular body defining a trash passageway; a fire door arrangement provided at a terminal end of the trash chute, the fire door arrangement including a door frame and a door slidably coupled to the door frame for closing the trash passageway during a fire; an aerosol discharge unit mounted to the door frame of the fire door arrangement, the discharge unit having an aerosol outlet in fluid communication with the trash passageway; a liquid diffusion appliance mounted remotely from the trash chute and the fire door arrangement, the liquid diffusion appliance including the compound in liquid form to be aerosolized and including a control system for operating the liquid diffusion appliance to generate the aerosolized compound from the liquid compound and discharge the aerosolized compound from an appliance outlet of the liquid diffusion appliance; and a conduit coupling the appliance outlet of the liquid diffusion appliance with the aerosol outlet of the discharge unit, the conduit defining an aerosol passageway through which the aerosolized compound travels to be discharged into the trash chute.

At least one embodiment of an installation method for treating a trash chute with an aerosolized compound may be summarized as including: mounting an aerosol discharge unit to a fire door arrangement provided at a terminal end of the trash chute, the discharge unit having an aerosol outlet that is in fluid communication with a trash passageway of the trash chute; mounting a liquid diffusion appliance remotely from the trash chute and the fire door arrangement, the liquid diffusion appliance including a compound in liquid form to be aerosolized and including a control system for operating the liquid diffusion appliance to generate an aerosolized compound from the liquid compound and to discharge the aerosolized compound from an appliance outlet of the liquid diffusion appliance; and coupling the appliance outlet of the liquid diffusion appliance to the aerosol outlet of the discharge unit via a conduit to enable the aerosolized compound to be generated by the remotely located liquid diffusion appliance and discharged into the trash passageway of the trash chute.

At least one embodiment of a kit for positioning a liquid diffusion appliance remote from a trash chute to be treated by an aerosolized compound discharged by the liquid diffusion appliance may be summarized as including: a multi-piece aerosol discharge unit including a base part and a separate nozzle part removably coupleable to the base part, wherein the nozzle part comprises a main body having a stem projecting from one side of the main body which includes an aerosol outlet, a fitting projecting from another side of the main body opposite the stem, and engagement features for removably coupling to corresponding features of the base part, wherein the base part includes an aperture through which the stem of the nozzle part extends for positioning the aerosol outlet in a position to discharge the aerosolized compound generated by the liquid diffusion appliance into the trash chute; and a conduit for coupling the liquid diffusion appliance to the aerosol discharge unit.

DETAILED DESCRIPTION

Figure 1:
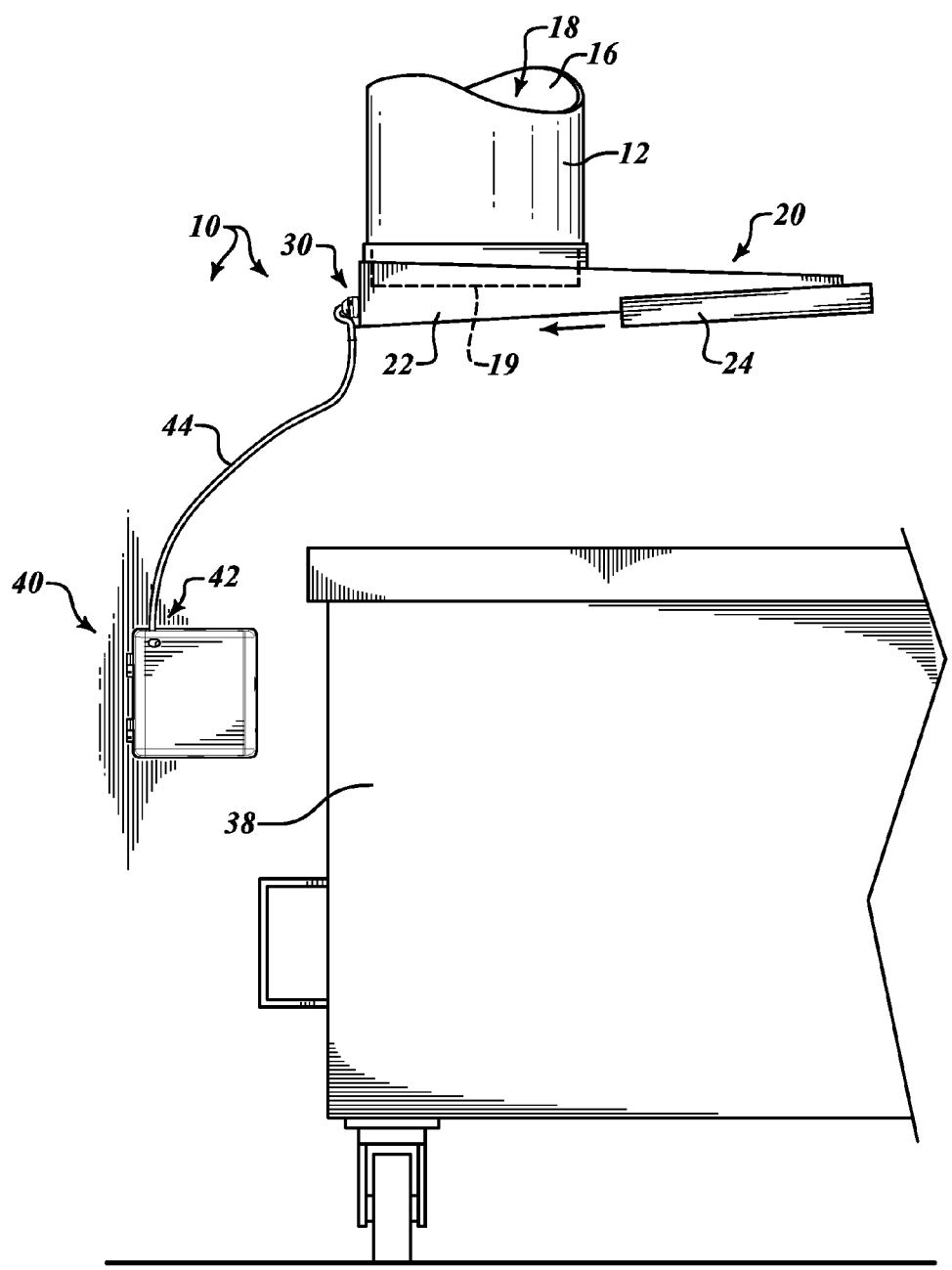
FIG. 1 is a side elevational view of an air treatment system, according to one embodiment, for treating a trash chute with an aerosolized compound.
Figure 2:
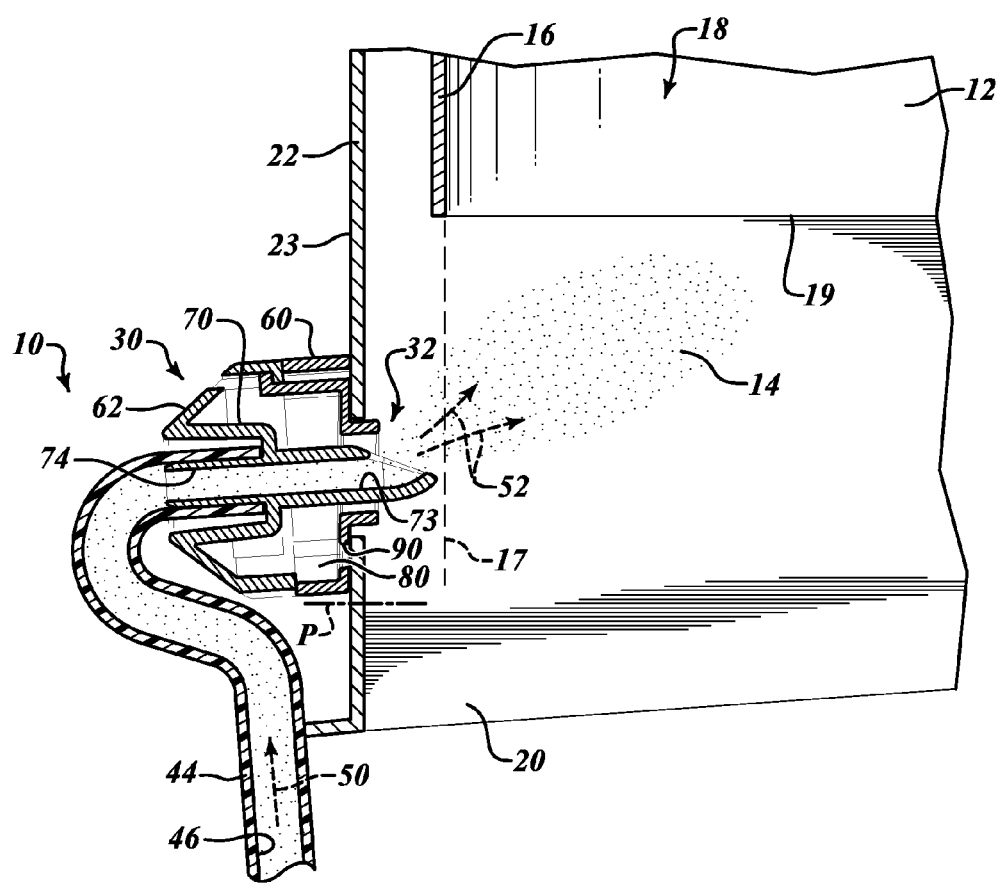
FIG. 2 is an enlarged cross-sectional side view of a discharge unit of the air treatment system of FIG. 1 mounted to a fire door arrangement of the trash chute and showing an aerosolized compound being discharged into a trash passageway of the trash chute.
Figure 3:
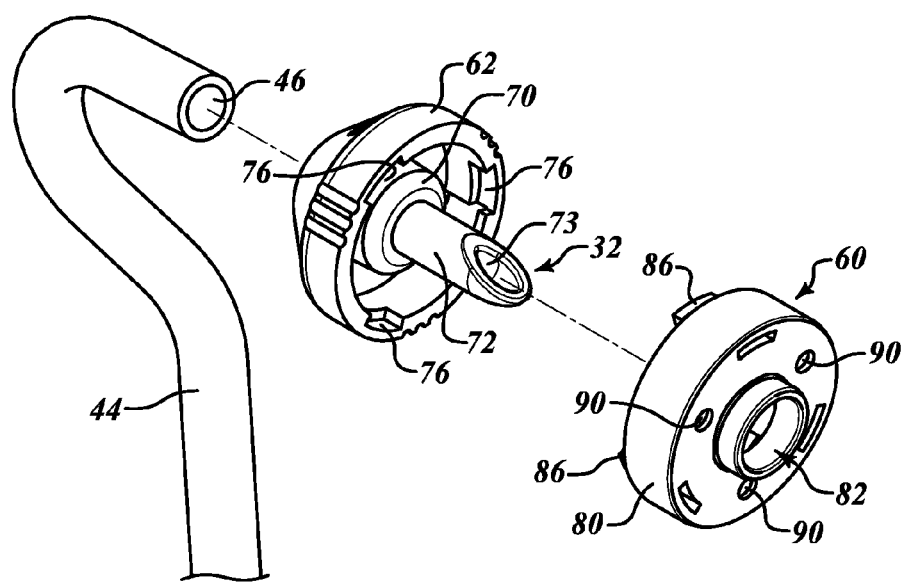
FIG. 3 is an isometric exploded view of the discharge unit of FIG. 2.

In the following description, certain specific details are set forth in order to provide a thorough understanding of various disclosed embodiments. However, one skilled in the relevant art will recognize that embodiments may be practiced without one or more of these specific details. In other instances, well-known devices, structures and techniques associated with liquid diffusion appliances, components thereof and related methods of diffusing liquid may not be shown or described in detail to avoid unnecessarily obscuring descriptions of the embodiments. Examples of liquid diffusion appliances and aspects and related methods thereof which may be used in combination with the systems described herein are shown in U.S. Pat. Nos. 7,712,683, 7,930,068 and 8,855,827, all of which are incorporated herein by reference in their entirety. Further examples of liquid diffusion appliances which may be used in combination with the systems described herein include commercial and residential liquid diffusion appliances, such as the 300 and 500 series appliances (e.g., AQ550 appliance) available from the present applicant, Prolitec Inc., of Milwaukee, Wis.

Unless the context requires otherwise, throughout the specification and claims which follow, the word "comprise" and variations thereof, such as "comprises" and "comprising," are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The present disclosure relates generally to air treatment systems and related methods and, more specifically, to air treatment systems and related methods for treating a trash chute with an aerosolized compound generated by a liquid diffusion appliance that is located remote from the trash chute.

The air treatment systems disclosed herein include or otherwise operate in conjunction with a liquid diffusion appliance to provide or introduce a pleasant or soothing scent (or some other type of liquid that may be used as an airborne treatment or compound) into the air space of a trash chute. The particular liquid to be dispensed by the liquid diffusion appliance may be contained within a removable cartridge within the liquid diffusion appliance. Other possible types of liquids that may be dispersed may include decontamination agents, insecticides, insect repellents, and many different types of liquids that may be desirably dispersed within an enclosed space. The present disclosure is not limited to a particular type or nature of liquid to be dispersed, but is intended to encompass any desirable airborne liquid treatments that are preferably dispersed within an enclosed space to be effective. The term enclosed space, as used herein, refers to any volume of space within which the atmospheric turnover is sufficiently slow to permit the dispersed liquid to have its desired effect within the space, and includes the trash passageway of a trash chute. Within the scope of the present disclosure, it is not intended to limit the nature, size or configuration of the trash chute to be treated or the nature, size or configuration of the fire door arrangement coupled thereto.

A source of pressurized gas (e.g., air) may be provided within or in connection with the liquid diffusion appliance that receives removable liquid cartridges. The source of pressurized gas may comprise, for example, a small air compressor or pump, an internal reservoir, or a connection to an external source of pressurized gas. Controls may be provided and configured to permit adjustment of the timing and/or pressure level of the pressurized gas (e.g., air) generated by the pump or compressor that is ultimately directed into and passes through the removable cartridge. Generally, the pressurized gas is directed to atomize the liquid contained in the removable cartridge and to aid in the dispersion of an aerosolized compound into the trash chute to be treated.

FIG. 1 shows one example embodiment of an air treatment system 10 for treating a trash chute 12 with an aerosolized compound 14 (FIG. 2). The air treatment system 10 includes or otherwise operates in conjunction with the trash chute 12, which includes a tubular body 16 defining a trash passageway 18, and has a fire door arrangement 20 provided at a terminal end thereof. The fire door arrangement 20 typically includes a door frame 22 and a door 24 slidably coupled to the door frame 22 for closing the trash passageway 18 during a fire for safety purposes. The air treatment system 10 further includes an aerosol discharge unit 30 mounted to the door frame 22 of the fire door arrangement 20 with an aerosol outlet 32 thereof in fluid communication with the trash passageway 18, as shown in FIG. 2. With reference to FIG. 1, the air treatment system 10 further includes a liquid diffusion appliance 40 which is mounted in a trash room containing a dumpster 38 or other garbage receptacle and in a location remote from the trash chute 12 and the fire door arrangement 20. The liquid diffusion appliance 40 includes a compound in liquid form to be aerosolized, such as liquid contained in a removable cartridge. A control system (not shown) is also provided for operating the liquid diffusion appliance 40 to generate the aerosolized compound 14 from the liquid compound and to discharge the aerosolized compound 14 from an appliance outlet 42 associated with the liquid diffusion appliance 40. A conduit 44 couples the appliance outlet 42 of the liquid diffusion appliance 40 with the aerosol outlet 32 of the discharge unit 30 and, with reference to FIG. 2, defines an aerosol passageway 46 through which the aerosolized compound 14 travels to be discharged into the trash chute 12, as represented by the arrows labeled 50, 52.

Further details of the discharge unit 30 of the air treatment system 10 are shown in FIGS. 2 and 3 for attaching to one type of fire door arrangement 20. Further details of a discharge unit 30' of a similar air treatment system 10' are shown in FIGS. 4 and 5 for attaching to a different type of fire door arrangement 20'.

According to some embodiments, and with reference to FIGS. 2 through 5, the aerosol discharge unit 30 may include a base part 60, 60' attached to the door frame 22, 22' of the fire door arrangement 20, 20' and a separate nozzle part 62 that is coupled to the base part 60, 60', the nozzle part 62 including the aerosol outlet 32. In some instances, the door frame 22 may include a vertical rear wall 23 and the base part 60 may have a tapered body 80 that abuts the vertical rear wall 23 to support the nozzle part 62 at an inclined orientation relative to a horizontal reference plane P, as shown, for example, in the illustrated embodiment of FIG. 2. In some instances, the door frame 22' may include an angle member 25 and the base part 60' may be removably secured to the angle member 25 via a snap-fit arrangement 88, as shown, for example, in the illustrated embodiment of FIG. 4. According to some embodiments, the base part 60' spaces the nozzle part 62 a distance below an outlet 19 of the trash passageway 18 in a location that does not obstruct operation of the fire door arrangement 20', as shown, for example, in the illustrated embodiment of FIG. 4. In some instances, the aerosol discharge unit 30, 30' may be mounted to the fire door arrangement 20 with the aerosol outlet 32 located about three to about six inches below the outlet 19 of the trash passageway 18. In some instances, the aerosol discharge unit 30, 30' may be mounted to the fire door arrangement 20, 20' with the aerosol outlet 19 located subsurface with respect to the trash passageway 18 (i.e., beyond the extended interior profile of the tubular body 16 of the trash chute 12) and not in the projected path of falling trash, as can be appreciated by each of the example embodiments shown in FIGS. 2 and 4. In some instances, the aerosol discharge unit 30, 30' may be mounted to the fire door arrangement 20, 20' with the aerosol outlet 32 located so as to extend no more than one-half inch into a projected path 17 of the trash passageway 18. In other instances, the aerosol discharge unit 30, 30' may be mounted to the fire door arrangement 20, 20' with the aerosol outlet 32 located so as to not extend into a projected path 17 of the trash passageway 18 at all.

According to some embodiments, including the illustrated embodiments of FIGS. 2 through 5, the aerosol discharge unit 30, 30' may include a nozzle or stem 72 comprising a nozzle passageway 73 that curves upwardly at a terminal end thereof to assist in directing the aerosolized compound 14 into the trash passageway 18. In some instances, the nozzle passageway 73 may be inclined relative to a horizontal reference plane P such that any liquid from the aerosolized compound 14 that condenses on surfaces of the nozzle passageway 73 drains away from the aerosol outlet 32 towards the liquid diffusion appliance 40. For example, the nozzle passageway 73 may be inclined at least four or five degrees relative to the horizontal reference plane P.

The liquid diffusion appliance 40 (FIG. 1) or removable cartridge thereof may include a diffusion head (not shown) including a venturi device for generating the aerosolized compound from the liquid compound as a stream of air moves through the venturi device to draw some of the liquid compound into the air stream. The aerosolized compound 14 may then be discharged from the appliance 40 to pass through the conduit 44 and the discharge unit 30, 30' to be discharged into the passageway 18 of the trash chute 12.

In view of the above, it will be appreciated that various methods of installation may be provided in connection with the air treatment systems 10, 10' disclosed herein. According to one example embodiment, an installation method may include: mounting an aerosol discharge unit 30, 30' to a fire door arrangement 20, 20' provided at a terminal end of a trash chute 12, the discharge unit 30, 30' having an aerosol outlet 32 that is in fluid communication with a trash passageway 18 of the trash chute 12; mounting a liquid diffusion appliance 40 remotely from the trash chute 12 and the fire door arrangement 20, 20', the liquid diffusion appliance 40 including a compound in liquid form to be aerosolized and including a control system for operating the liquid diffusion appliance 40 to generate an aerosolized compound 14 from the liquid compound and to discharge the aerosolized compound 14 from an appliance outlet 42 of the liquid diffusion appliance 40; and coupling the appliance outlet 42 of the liquid diffusion appliance 40 to the aerosol outlet 32 of the discharge unit 30, 30' via a conduit 44 to enable the aerosolized compound 14 to be generated by the remotely located liquid diffusion appliance 40 and discharged into the trash passageway 18 of the trash chute 12.

The fire door arrangement 20, 20' may include a door frame 22, 22' and a door 24 slidably coupled to the door frame 22, 22' for closing the trash passageway 18 during a fire, and mounting the aerosol discharge unit 30, 30' to the fire door arrangement 20, 20' may include coupling the discharge unit 30, 30' to the door frame 22, 22' of the fire door arrangement 20, 20' in a position so as to not obstruct operation of the door 24. Mounting the aerosol discharge unit 30, 30' to the fire door arrangement 20, 20' may include attaching a base part 60, 60' of the aerosol discharge unit 30, 30' to the door frame 22, 22' and removably securing a separate nozzle part 62 of the aerosol discharge unit to the base part 60, 60', the nozzle part 62 comprising the aerosol outlet 32. Mounting the aerosol discharge unit 30, 30' to the fire door arrangement 20, 20' may include coupling the discharge unit 30, 30' to the fire door arrangement 20, 20' so as not to extend into a projected path of trash descending through the trash passageway 18. Mounting the aerosol discharge unit 30, 30' to the fire door arrangement 20, 20' may include coupling the discharge unit 30, 30' to the fire door arrangement 20, 20' so as to extend no more than one-half inch into a projected path 17 of the trash passageway 18. Mounting the aerosol discharge unit 30, 30' to the fire door arrangement 20, 20' may include coupling the discharge unit 30, 30' to the fire door arrangement 20, 20' with a nozzle passageway 73 of the aerosol discharge unit 30, 30' inclined relative to a horizontal reference plane P.

With reference to FIGS. 1 through 5, a kit may be provided for treating a trash chute 12 with an aerosolized compound 14. The kit may include: a multi-piece aerosol discharge unit 30, 30' comprising a base part 60, 60' and a separate nozzle part 62 removably coupleable to the base part 60, 60', and a conduit 44 for coupling a liquid diffusion appliance 40 to the aerosol discharge unit 30, 30'. The nozzle part 62 may comprise a main body 70 having a nozzle or stem 72 projecting from one side of the main body 70, which includes an aerosol outlet 32, a fitting 74 projecting from another side of the main body 70 opposite the stem 72, and engagement features 76 (e.g., keyways) for removably coupling to corresponding features 86, 86' (e.g., keys) of the base part 60, 60'. The base part 60, 60' may include an aperture 82, 82' through which the stem 72 of the nozzle part 62 extends for positioning the aerosol outlet 32 in a position to discharge the aerosolized compound 14 generated by the liquid diffusion appliance 40 into the trash chute 12. In some instances, the base part 60, 60' of the aerosol discharge unit 30, 30' may have a plurality of apertures 90, 90' through which fasteners (e.g., machine screws) may be received for fastening the base part 60 to the fire door arrangement 20, 20'. In some instances, the base part 60 of the aerosol discharge unit 30 may have a tapered body 80 that is configured to abut a vertical rear wall 23 of a fire door frame 22 at a terminal end of the trash chute 12 to support a nozzle passageway 73 of the nozzle part 62 at an inclined orientation relative to a horizontal reference plane P, as shown, for example, in the illustrated embodiment of FIG. 2.

Figure 4:
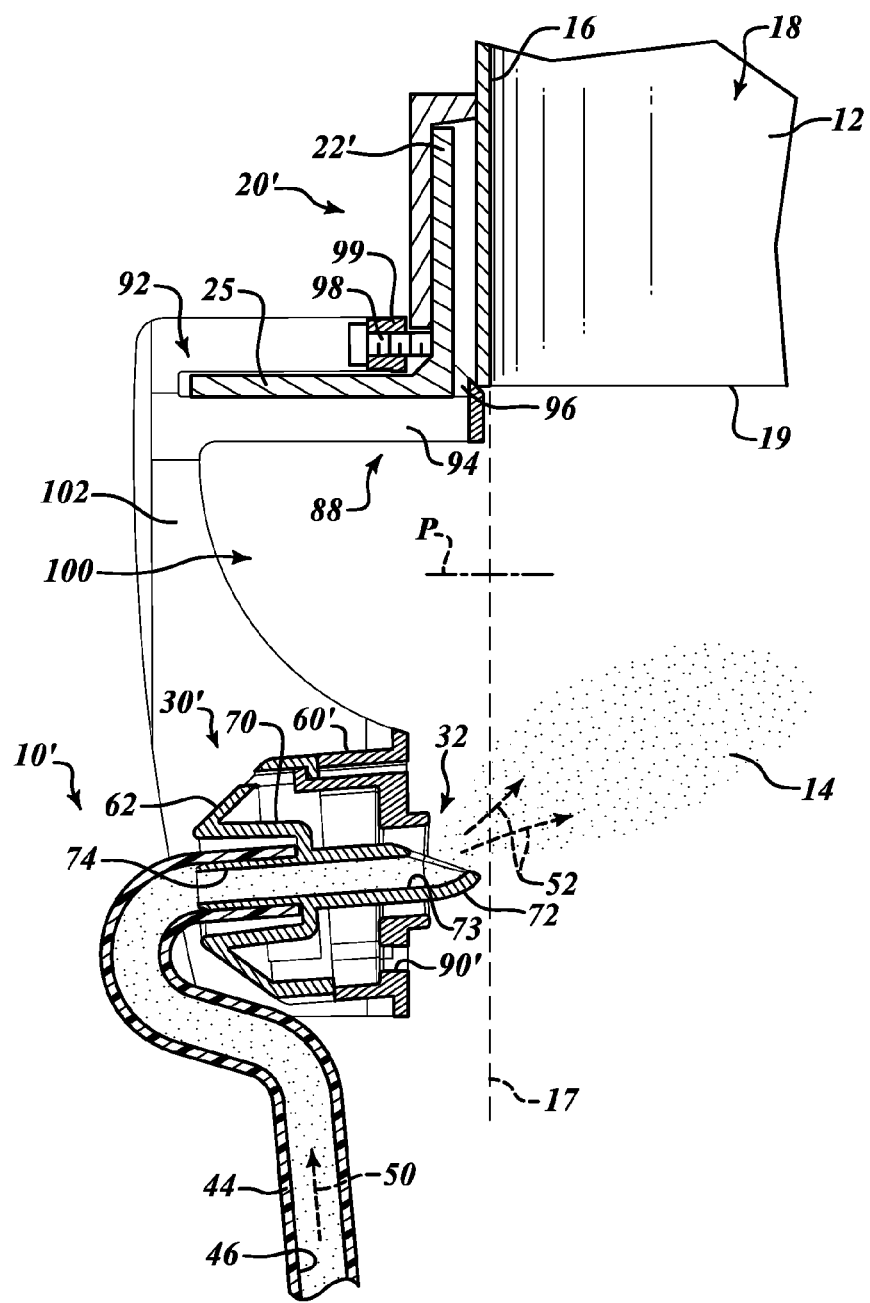
FIG. 4 is an enlarged cross-sectional side view of a discharge unit of an air treatment system, according to another embodiment, showing an aerosolized compound being discharged into a trash passageway of the trash chute.
Figure 5:
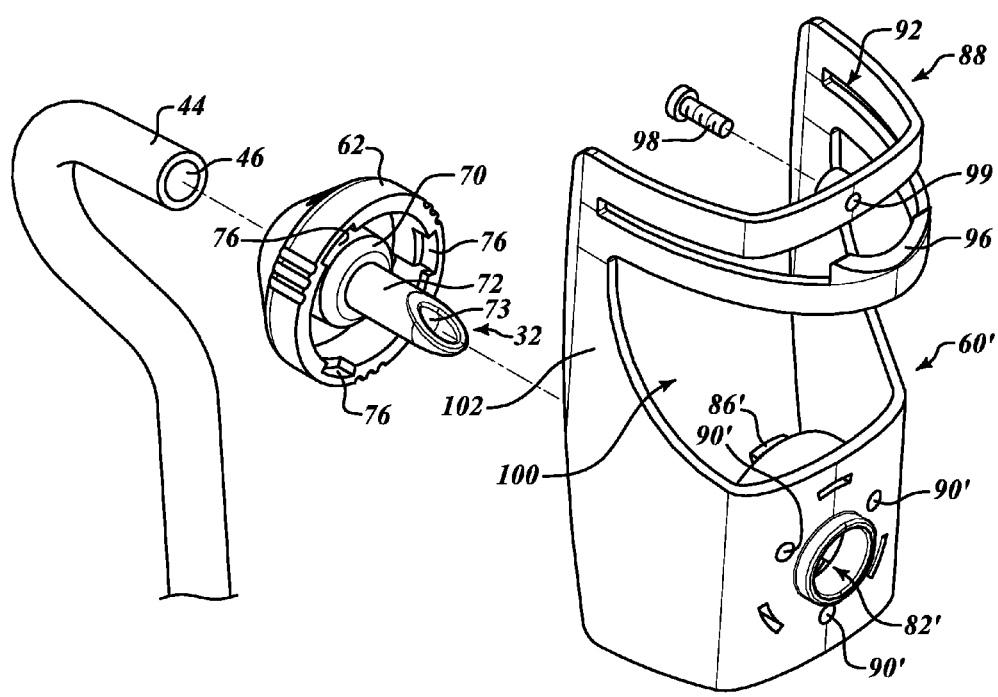
FIG. 5 is an isometric exploded view of the discharge unit of FIG. 4.

In some instances, the base part 60' of the aerosol discharge unit 30' may comprise a snap-fit arrangement 88 for coupling to an angle member 25 of a fire door frame 22' at a terminal end of the trash chute 12 to support a nozzle passageway 73 of the nozzle part 62 at an inclined orientation relative to a horizontal reference plane P, as shown in FIG. 4. For example, the snap-fit arrangement 88 may include a channel 92 or other cavity to receive a portion of the fire door arrangement 20', and a flexible portion or portions 94 of the base part 60' may be configured to flex to enable the portion of the fire door arrangement 20' to be received in the channel 92 or other cavity. A catch or stop 96 may be provided to assist in retaining the portion of the fire door arrangement 20' in the channel 92 or other cavity of the base part 60' once the base part 60' is snapped or clipped onto the fire door arrangement 20'. In addition, a set screw 98 or other retaining device may be provided for further securing the aerosol discharge unit 30' to the fire door arrangement 20'. The set screw 98 may pass through a corresponding aperture 99 in the base part 60' and engage the fire door arrangement 20' to secure the aerosol discharge unit 30' to the fire door arrangement 20' and prevent incidental dislodgement of the aerosol discharge unit 30'. With reference to FIGS. 4 and 5, the snap-fit arrangement of the base part 60' may be provided at an upper end with the nozzle passageway 73 and the aerosol outlet 32 provided at a lower end, and a clearance gap or space 100 may be provided therebetween for enabling the aerosol discharge unit 30' to be mounted in the vicinity of the fire door arrangement 20' without obstructing operation of the same. The clearance gap or space 100 may define a reduced neck portion 102 of the base part 60'.

The multi-piece aerosol discharge unit 30, 30' of the kit may include a plurality of different base parts 60, 60', and one or more separate nozzle parts 62 may interface with each of the different base parts 60, 60' to form different mounting arrangements to accommodate a variety of different fire door arrangements 20, 20'. In any event, the kit may be used to route aerosolized matter (i.e., aerosolized compound 14) from a remotely located liquid diffusion appliance 40 to an area adjacent the terminal end of a trash chute 12 without interfering with trash moving through the trash chute 12, without interfering with operation of a fire door arrangement 20, 20' coupled to the trash chute 12, and without jeopardizing the integrity of the trash chute 12 itself, such as would otherwise occur if piercing the trash chute 12.

Aspects and features of the various embodiments described above may also be combined to provide further embodiments. All of the U.S. patents, U.S. patent application publications, U.S. patent applications, foreign patents, foreign patent applications and non-patent publications referred to in this specification and/or listed in the Application Data Sheet, including US Provisional Patent Application No. 62/220,139, filed Sep. 17, 2015, are incorporated herein by reference, in their entirety. Aspects of the embodiments can be modified, if necessary to employ features, structures, functionality or concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A system for treating a trash chute with an aerosolized compound, the system comprising:
a trash chute having a tubular body defining a trash passageway;
a fire door arrangement provided at a terminal end of the trash chute, the fire door arrangement including a door frame and a door slidably coupled to the door frame for closing the trash passageway during a fire;
an aerosol discharge unit mounted to the door frame of the fire door arrangement, the aerosol discharge unit having an aerosol outlet in fluid communication with the trash passageway;
a liquid diffusion appliance mounted remotely from the trash chute and the fire door arrangement, the liquid diffusion appliance including the compound in liquid form to be aerosolized and including a control system for operating the liquid diffusion appliance to generate the aerosolized compound from the liquid compound and discharge the aerosolized compound from an appliance outlet of the liquid diffusion appliance; and
a conduit coupling the appliance outlet of the liquid diffusion appliance with the aerosol outlet of the aerosol discharge unit, the conduit defining an aerosol passageway through which the aerosolized compound travels to be discharged into the trash chute.

2. The system of claim 1 wherein the aerosol discharge unit includes a base part attached to the door frame of the fire door arrangement and a separate nozzle part that is coupled to the base part, the nozzle part including the aerosol outlet.

3. The system of claim 2 wherein the door frame includes a vertical rear wall and the base part has a tapered body that abuts the vertical rear wall to support the nozzle part at an inclined orientation relative to a horizontal reference plane.

4. The system of claim 2 wherein the door frame includes an angle member and the base part is removably secured to the angle member via a snap-fit arrangement.

5. The system of claim 2 wherein the base part spaces the nozzle part a distance below an outlet of the trash passageway in a location that does not obstruct operation of the fire door arrangement.

6. The system of claim 1 wherein the aerosol discharge unit is mounted to the fire door arrangement with the aerosol outlet located about three to about six inches below an outlet of the trash passageway.

7. The system of claim 1 wherein the aerosol discharge unit is mounted to the fire door arrangement with the aerosol outlet located subsurface with respect to the trash passageway and not in a projected path of falling trash.

8. The system of claim 1 wherein the aerosol discharge unit is mounted to the fire door arrangement with the aerosol outlet located so as to extend no more than one-half inch into a projected path of the trash passageway.

9. The system of claim 1 wherein the aerosol discharge unit is mounted to the fire door arrangement with the aerosol outlet located so as to not extend into a projected path of the trash passageway.

10. The system of claim 1 wherein the aerosol discharge unit includes a nozzle comprising a nozzle passageway that curves upwardly at a terminal end thereof to assist in directing the aerosolized compound into the trash passageway.

11. The system of claim 1 wherein the aerosol discharge unit includes a nozzle comprising the aerosol outlet and a nozzle passageway extending through the nozzle, the nozzle passageway being inclined relative to a horizontal reference plane such that any liquid from the aerosolized compound that condenses on surfaces of the nozzle passageway drains away from the aerosol outlet towards the liquid diffusion appliance.

12. The system of claim 11 wherein the nozzle passageway is inclined relative to the horizontal reference plane.

13. The system of claim 1 wherein the liquid diffusion appliance includes a diffusion head including a venturi device for generating the aerosolized compound from the liquid compound as a stream of air moves through the venturi device to draw in some of the liquid compound into the stream of air.

14. An installation method, comprising:
mounting an aerosol discharge unit to a fire door arrangement provided at a terminal end of a trash chute, the aerosol discharge unit having an aerosol outlet that is in fluid communication with a trash passageway of the trash chute;
mounting a liquid diffusion appliance remotely from the trash chute and the fire door arrangement, the liquid diffusion appliance including a compound in liquid form to be aerosolized and including a control system for operating the liquid diffusion appliance to generate an aerosolized compound from the liquid compound and to discharge the aerosolized compound from an appliance outlet of the liquid diffusion appliance; and
coupling the appliance outlet of the liquid diffusion appliance to the aerosol outlet of the aerosol discharge unit via a conduit to enable the aerosolized compound to be generated by the remotely located liquid diffusion appliance and discharged into the trash passageway of the trash chute.

15. The installation method of claim 14 wherein the fire door arrangement includes a door frame and a door slidably coupled to the door frame for closing the trash passageway during a fire, and wherein mounting the aerosol discharge unit to the fire door arrangement includes coupling the aerosol discharge unit to the door frame of the fire door arrangement in a position so as to not obstruct operation of the door.

16. The installation method of claim 15 wherein mounting the aerosol discharge unit to the fire door arrangement includes attaching a base part of the aerosol discharge unit to the door frame and removably securing a separate nozzle part of the aerosol discharge unit to the base part, the nozzle part comprising the aerosol outlet.

17. The installation method of claim 14 wherein mounting the aerosol discharge unit to the fire door arrangement includes coupling the aerosol discharge unit to the fire door arrangement so as not to extend into a projected path of trash descending through the trash passageway.

18. The installation method of claim 14 wherein mounting the aerosol discharge unit to the fire door arrangement includes coupling the aerosol discharge unit to the fire door arrangement with a nozzle of the aerosol discharge unit inclined relative to a horizontal reference plane.

19. A kit for positioning a liquid diffusion appliance remote from a trash chute to be treated by an aerosolized compound generated by the liquid diffusion appliance, the kit comprising:
    a multi-piece aerosol discharge unit including a base part and a separate nozzle part removably coupleable to the base part,
    wherein the nozzle part comprises a main body having a stem projecting from one side of the main body which includes an aerosol outlet, a fitting projecting from another side of the main body opposite the stem, and engagement features for removably coupling to corresponding features of the base part,
    wherein the base part includes an aperture through which the stem of the nozzle part extends for positioning the aerosol outlet in a position to discharge the aerosolized compound generated by the liquid diffusion appliance into the trash chute; and
    a conduit for coupling the liquid diffusion appliance to the aerosol discharge unit.

20. The kit of claim 19 wherein the base part of the aerosol discharge unit has a tapered body that is configured to abut a vertical rear wall of a fire door frame at a terminal end of the trash chute to support a nozzle passageway of the nozzle part at an inclined orientation relative to a horizontal reference plane.

21. The kit of claim 19 wherein the base part of the aerosol discharge unit comprises a snap-fit arrangement for coupling to an angle member of a fire door frame at a terminal end of the trash chute to support a nozzle passageway of the nozzle part at an inclined orientation relative to a horizontal reference plane.

\* \* \* \* \*